United States Patent [19]
Bilkhu et al.

[11] Patent Number: 5,493,898
[45] Date of Patent: Feb. 27, 1996

[54] HYDROSTATIC TESTING OF CRUSHABLE FOAMS

[75] Inventors: Sukhbir S. Bilkhu, Rochester Hills; Dale A. Bode, Wixom; Lawrence Zukowski, Madison Heights, all of Mich.

[73] Assignee: Chrysler Corporation, Highland Park, Mich.

[21] Appl. No.: 334,993

[22] Filed: Nov. 7, 1994

[51] Int. Cl.$^6$ .................................................. G01M 3/02
[52] U.S. Cl. ........................................................ 73/37; 73/38
[58] Field of Search .................................... 73/36, 37, 38, 73/798, 797, 796

[56] References Cited

U.S. PATENT DOCUMENTS

| | | | |
|---|---|---|---|
| 3,535,922 | 10/1970 | Pocock | 73/94 |
| 3,955,406 | 5/1976 | Strydom | 73/78 |
| 4,513,603 | 4/1985 | Baillie | 73/37 |
| 4,679,441 | 7/1987 | Johnson et al. | 73/798 |
| 5,299,453 | 4/1994 | Sprunt et al. | 73/38 |
| 5,365,793 | 11/1994 | Terrel et al. | 73/38 |

*Primary Examiner*—Richard Chilcot
*Assistant Examiner*—Max Noori
*Attorney, Agent, or Firm*—Margaret A. Dobrowitsky

[57] ABSTRACT

A system for hydrostatically measuring the volumetric deformation of a crushable foam includes a test chamber that is in fluid communication with a pressure fluid reservoir. A sample of a crushable foam is loaded within the test chamber within a latex pouch and the pressure fluid is pumped into the test chamber in order to subject the foam sample to triaxial loading. The volumetric deformation of the crushable foam is continuously monitored through suitable electronics as a function of pressure within the system.

15 Claims, 1 Drawing Sheet

HYDROSTATIC TESTING OF CRUSHABLE FOAMS

BACKGROUND OF THE INVENTION

1. Field of the Invention

This invention relates generally to a device for testing the crushability of materials, and more specifically to a device for measuring the volumetric deformation of a crushable foam under triaxial loading as a function of pressure.

2. Description of the Prior Art

Various devices for testing the deformability or hardness of materials such as soil samples or cigarettes include several shortcomings and drawbacks. For example, some systems use an arrangement where a piston moves inward into a fluid-filled container in order to increase the pressure within the container to thereby crush material such as rock, salt, ice or concrete. In such systems, two main drawbacks exist. First, it may be difficult to maintain enough pressure on the piston external from the fluid-filled chamber in order to increase the amount of pressure within the chamber in a desired fashion. Second, movement of the piston into the fluid-filled chamber undesirably changes the confining pressure within the chamber; under some conditions it may be desirable to maintain a constant pressure within a pressurized chamber.

Other devices for testing the hardness of a cigarette, for example, include the use of pneumatic suction applied to the interior of a cigarette. The volumetric change of the cigarette under the suction is measured. In such systems, the outer diameter of the cigarette is measured before and after the suction is applied. Significant drawbacks in such systems are present because the methodology requires relatively sophisticated and costly equipment that is only usable by skilled personnel under very controlled laboratory conditions. Further, a continuous measurement of deformation is unattainable.

This invention provides a system for measuring the volumetric change or crushability of a crushable foam that overcomes the drawbacks and shortcomings of the prior art just described. Accordingly, it is a primary object of this invention to provide a system for continuously measuring the crushability of a crushable foam under triaxial loading in an efficient, cost-effective manner.

SUMMARY OF THE INVENTION

In most general terms, this invention provides a device for measuring the volumetric deformability or crushability of materials such as foam.

This invention provides a device that includes a reservoir of pressure fluid. A test chamber is connected to the reservoir such that there is fluid communication between the two. The test chamber is adapted to contain a piece of crushable material. A means for transferring preselected amounts of pressure fluid from the reservoir to the test chamber alters the fluid pressure within the test chamber. The change in fluid pressure within the test chamber causes a volumetric deformation in the piece of material because the test chamber has fixed interior dimensions (i.e., a fixed interior volume capacity). Lastly, a means is provided to determine the volumetric deformation of the piece of material as a function of the fluid pressure within the test chamber.

In the preferred embodiment, a latex pouch is disposed within the test chamber to hold the piece of material within the chamber while preventing it from getting wet. An air passage is preferably provided to allow trapped air to escape from the pouch while the crushable material undergoes a volumetric deformation.

These and other features and advantages of this invention will become apparent to those skilled in the art from the following detailed description taken in connection with the accompanying drawings.

DETAILED DESCRIPTION OF THE PREFERRED EMBODIMENTS

Figure 1:
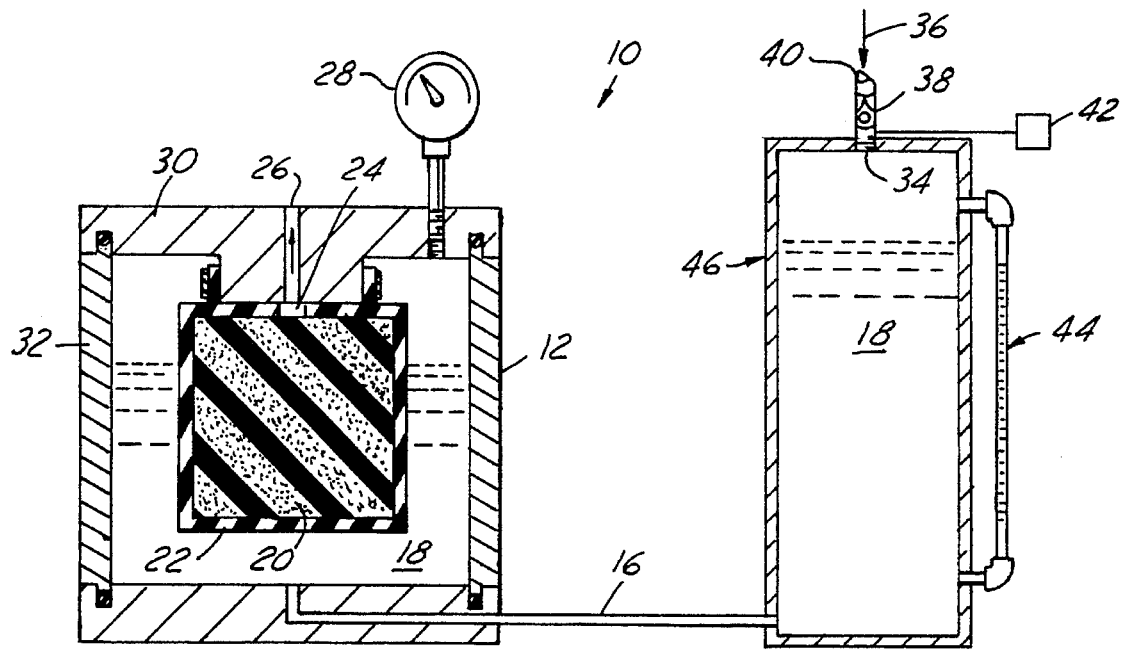
FIG. 1 is a partial cross-sectional diagrammatic representation of a device in accordance with this invention for the hydrostatic testing of crushable foams.
Figure 2:
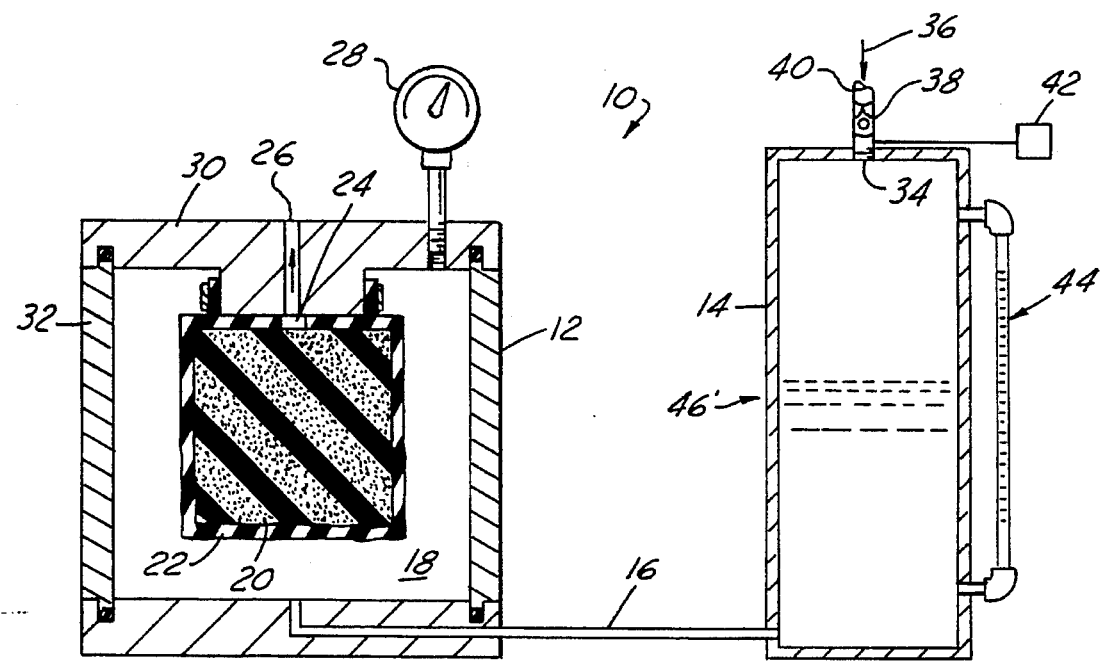
FIG. 2 is a partial cross-sectional view of the device of FIG. 1 showing a foam sample under different pressure conditions than illustrated in FIG. 1.

FIGS. 1 and 2 show the system 10 of the present invention for hydrostatically testing the crushability of a crushable foam or like material. System 10 includes a test chamber 12 and a fluid reservoir 14 coupled by a conduit 16 that allows pressure fluid 18 to be communicated between chamber 12 and reservoir 14. Pressure fluid 18 can be water or another liquid, although water is preferred because of its environmental compatibility, relative availability and because it is generally considered a noncorrosive fluid for applications such as that used in connection with this invention. A sample of crushable foam 20 is disposed within test chamber 12 and resides within a latex pouch 22. Foam sample 20, as illustrated in the drawings, is a cubic piece of a crushable foam material. Cubic foam sample 20 is subjected to triaxial loading by the pressure fluid 18 within test chamber 12. Triaxial loading can be appreciated as applied to a cubic piece of material by considering the load applied along the three orthogonal axes running from front-to-back, side-to-side and top-to-bottom, respectively.

Latex pouch 22 includes opening 24 that is in pneumatic communication with opening 26 in test chamber 12. Opening 24 and opening 26 facilitate the release of trapped air from within pouch 22 that would otherwise distort the measurement of the volumetric deformation of crushable foam 20.

Test chamber 12, as illustrated, also includes a pressure gauge 28 for visually indicating the amount of pressure exerted upon foam sample 20 by the pressure fluid 18 within test chamber 12. A piece of crushable foam 20 is preferably placed within a latex pouch 22 and then placed within test chamber 12 prior to allowing pressure fluid 18 to be introduced into test chamber 12. Accordingly, test chamber 12 is provided with a top panel 30 that is removable. Alternatively, side panels 32 can be removed in order to facilitate placing latex pouch 22 and foam sample 20 within test chamber 12.

Fluid reservoir 14 has an air inlet 34 for allowing pressured air to be delivered into reservoir 14 as illustrated diagrammatically by arrow 36. A check valve 38, illustrated as a conventional ball and seat valve, is placed within air tube 40 in order to maintain the pressure being applied within the system 10 in a controlled fashion. A pressure transducer 42 is schematically illustrated coupled to air inlet tube 40 between check valve 38 and air inlet 34. Pressure transducer 42 is a conventional electronic pressure transducer that facilitates monitoring pressure applied by the air flow 36 and maintained within the system 10. Pressure transducer 42 enables the user of a system designed in accordance with this invention to couple the system to a conventional microprocessor or computer to thereby provide a continuous, instanteous readout of the pressure maintained within system 10 to thereby continuously monitor the volumetric deformation of crushable foam sample 20 as a function of pressure.

Test chamber 14 also includes a displacement transducer illustrated diagrammatically at 44. Displacement transducer 44 is a conventional device that facilitates continuously monitoring the displacement of pressure fluid 18 from reservoir 14 into test chamber 12. Similarly, a scale is alternatively provided along one side of reservoir 14 to visually or otherwise indicate the level of pressure fluid 18 maintained within reservoir 14 under any given pressure conditions. Displacement transducer 44 is preferably coupled to a conventional microprocessor or computer. The displacement information is preferably correlated with the information gathered from pressure transducer 42 in order to provide a systematic measurement of the volumetric deformation of crushable foam 20 as a function of pressure and/or displacement of pressure fluid 18.

System 10 works in the following general manner. A sample of crushable foam 20 is placed within latex pouch 22 which is then, in turn, placed within test chamber 12. Pressurized air 36 is fed into reservoir 14 in order to force pressure fluid 18 into test chamber 12. FIG. 1 illustrates a condition wherein the pressure fluid 18 is at a first level 46 within reservoir 14, which corresponds to test chamber 12 not being completely filled with pressure fluid 18. FIG. 2 illustrates a "later" condition that includes pressure fluid 18 being at a second level 46' within reservoir 14. When pressure fluid 18 is at second level 46' within reservoir 14, test chamber 12 is completely filled with pressure fluid 18 and the amount of pressure exerted upon crushable foam 20 causes a volumetric deformation in the crushable foam 20. The interior of test chamber 12 has fixed dimensions. Therefore, a fixed maximum volume is maintained within the interior of test chamber 12. At an early stage, the total volume within test chamber 12 is occupied by fluid 18, foam sample 20 and air that is trapped within latex pouch 22. As more fluid 18 is forced into test chamber 12, foam sample 20 responsively undergoes a volumetric deformation once any excess trapped air is released through openings 24 and 26. In other words, as more air is supplied under pressure through inlet 34, the pressure within test chamber 12 proportionally increases and the increased pressure induces axial loading along all three axes of cubic foam sample 20.

The amount of volumetric deformation of foam sample 20 is calculated by the knowledge or ascertainment of the pressure within test chamber 12 and the amount of fluid displacement of pressure fluid 18 from reservoir 14 into test chamber 12. The amount of fluid displacement gives some volumetric information and the pressure within chamber 12 is used in combination with the displacement information to ensure an accurate determination of volumetric deformation of the foam sample 20.

Displacement transducer 44 provides a reading of the amount of fluid displacement between reservoir 14 and test chamber 12 and pressure transducer 42 provides a continuous, instantaneous measurement of the pressure exerted within the system 10. The relationship between the volumetric deformation of foam 20, the amount of fluid displacement of pressure fluid 18 and the pressure within system 10 can be determined through suitable electronics by manipulating electronic signals generated by pressure transducer 42 and displacement transducer 44.

The preceding description is exemplary rather than limiting in nature. Variations and modifications will become apparent to those skilled in the art that do not depart from the purview and spirit of this invention. The scope of this invention is to be limited only by the appended claims including all fair legal equivalents.

We claim:

1. A device for measuring the volumetric deformability of a crushable material, comprising:

a reservoir for containing a pressure fluid;

a test chamber having an interior chamber that defines a fixed chamber volume in fluid communication with said reservoir;

a latex pouch holder deformable in three orthogonal axes for holding a piece of crushable material within said interior chamber and for preventing the piece of material from contacting said pressure fluid;

means for transferring preselected amounts of pressure fluid from said reservoir to said interior chamber, said pressure fluid altering a fluid pressure within said interior chamber, said fluid pressure acting through said pouch holder for subjecting said piece of crushable material to loading in said three orthogonal axes to thereby cause a volumetric deformation in the piece of crushable material; and means for determining the volumetric deformation of the piece of crushable material as a function of the fluid pressure within said interior chamber.

2. The device of claim 1, wherein said test chamber has a plurality of sidewalls that establish a top, bottom and sides of said test chamber and wherein at least one said sidewall is removable to facilitate placing the piece of crushable material within said interior chamber.

3. The device of claim 2, wherein said test chamber further comprising an outlet in pneumatic communication with an opening in said holder for allowing air to escape from within said holder as the piece of crushable material undergoes a volumetric deformation.

4. The device of claim 1, wherein said transferring means comprises an inlet into said reservoir and an air pressure source for forcing pressurized air into said reservoir to thereby force a portion of said pressure fluid into said interior chamber.

5. The device of claim 1, wherein said determining means comprises a pressure transducer coupled to said device for detecting a pressure within the device and producing an output signal that is indicative of said pressure.

6. The device of claim 5, wherein said pressure transducer is coupled to an air inlet tube coupled to said reservoir and wherein said transducer detects an amount of air pressure delivered into said reservoir through said air inlet tube to thereby indicate a fluid pressure within said interior chamber.

7. The device of claim 1, wherein said determining means comprises a displacement transducer coupled to said reservoir such that said displacement transducer detects the amount of pressure fluid that is displaced from said reservoir into said interior chamber.

8. The device of claim 1, wherein said determining means comprises a pressure transducer coupled to said device that detects a pressure within said interior chamber and generates a first electrical signal indicative of said pressure, said determining means further comprising a displacement transducer coupled to said device that detects an amount of fluid that is displaced into said interior chamber and generates a second electrical signal indicative of said amount, whereby the volumetric deformation of the piece of crushable material is determined as a function of said first and second electrical signals.

9. A device for determining the volumetric deformation of a piece of crushable material as a function of pressure, comprising:

a first chamber for containing a fluid;

a second chamber having fixed interior dimensions, and being in fluid communication with said first chamber;

a latex pouch holder deformable in three orthogonal axes for holding the piece of crushable material within said second chamber;

a source of pressure for transferring preselected amounts of fluid from said first chamber to said second chamber, said fluid altering a fluid pressure within said second chamber, said fluid pressure acting through said pouch holder for subjecting said piece of crushable material to loading in said three orthogonal axes to thereby cause a volumetric deformation in the piece of crushable material; and means for determining the volumetric deformation of the piece of crushable material as a function of the fluid pressure within said second chamber.

10. The device of claim 9, wherein said second chamber comprises a plurality of panels and one of said panels is selectively removable to facilitate placing the piece of crushable material within said second chamber.

11. The device of claim 9, wherein said test chamber further comprises an outlet in pneumatic communication with an opening in said holder for allowing air to escape from within said holder as the piece of crushable material undergoes a volumetric deformation.

12. The device of claim 9, wherein said source of pressure comprises an inlet into said first chamber and an air pressure source for forcing pressurized air into said first chamber to thereby force an amount of said fluid into said second chamber.

13. The device of claim 9, wherein said determining means comprises a pressure transducer coupled to said device for detecting a pressure within the device and producing an output signal that is indicative of the pressure within said second chamber.

14. The device of claim 9, wherein said determining means comprises a displacement transducer coupled to said first chamber such that said displacement transducer detects the amount of fluid that is displaced from said first chamber into said second chamber.

15. The device of claim 9, wherein said determining means comprises a pressure transducer coupled to said device that detects a pressure within said device and generates a first electrical signal indicative of the pressure within said second chamber, said determining means further comprising a displacement transducer coupled to said device that detects an amount of fluid that is displaced into said second chamber and generates a second electrical signal indicative of said amount, whereby the volumetric deformation of the piece of crushable material is determined as a function of said first and second electrical signals.

* * * * *